United States Patent
Eberhart et al.

(10) Patent No.: US 8,717,141 B2
(45) Date of Patent: May 6, 2014

(54) DEVICE AND METHOD FOR IDENTIFYING A USER OF A MEDICAL DEVICE

(75) Inventors: Andreas Eberhart, Oberburg (CH); Hanspeter Heiniger, Lotzwil (CH); Erich Imhof, Utzenstorf (CH); Thomas Rufer, Ostermundigen (CH)

(73) Assignee: Roche Diagnostics International AG, Rotkreuz (CH)

( * ) Notice: Subject to any disclaimer, the term of this patent is extended or adjusted under 35 U.S.C. 154(b) by 1790 days.

(21) Appl. No.: 11/293,468

(22) Filed: Dec. 2, 2005

(65) Prior Publication Data

US 2006/0132283 A1    Jun. 22, 2006

Related U.S. Application Data

(63) Continuation of application No. PCT/EP2004/005038, filed on May 11, 2004.

(30) Foreign Application Priority Data

Jun. 3, 2003   (DE) .................................. 103 25 106

(51) Int. Cl.
*G06K 9/00*      (2006.01)
*A61M 5/14*     (2006.01)
*A61B 18/14*    (2006.01)
*G06F 17/00*    (2006.01)

(52) U.S. Cl.
USPC .................... 340/5.2; 340/539.12; 340/573.1; 340/5.8

(58) Field of Classification Search
CPC ........... G06K 9/00; A61M 5/14; A61B 18/14; G06F 17/00

USPC ............ 340/5.2, 539.12, 5.8, 573.1; 382/128; 705/3; 707/3; 713/186, 156, 176; 604/66; 606/41, 34, 42

See application file for complete search history.

(56) References Cited

U.S. PATENT DOCUMENTS

| | | | | |
|---|---|---|---|---|
| 4,857,713 A * | 8/1989 | Brown | .............................. | 705/3 |
| 4,978,335 A * | 12/1990 | Arthur, III | ........................ | 604/67 |
| 5,276,610 A * | 1/1994 | Maeda et al. | ............... | 604/890.1 |
| 5,630,710 A * | 5/1997 | Tune et al. | .................... | 417/326 |
| 5,755,563 A * | 5/1998 | Clegg et al. | ................... | 417/326 |
| 5,936,523 A | 8/1999 | West | | |
| 6,148,094 A * | 11/2000 | Kinsella | ........................ | 382/124 |
| 6,241,724 B1 * | 6/2001 | Fleischman et al. | ............ | 606/41 |
| 6,269,340 B1 * | 7/2001 | Ford et al. | ......................... | 705/3 |
| 6,358,225 B1 * | 3/2002 | Butterfield | ....................... | 604/65 |
| 6,401,987 B1 * | 6/2002 | Oechsel et al. | ............ | 222/321.7 |
| 6,423,035 B1 * | 7/2002 | Das et al. | ....................... | 604/155 |
| 6,485,465 B2 * | 11/2002 | Moberg et al. | ................... | 604/67 |
| 6,505,193 B1 * | 1/2003 | Musgrave et al. | ................. | 707/3 |

(Continued)

FOREIGN PATENT DOCUMENTS

| | | |
|---|---|---|
| EP | 0980688 A | 2/2000 |
| JP | 2002-165881 | 6/2002 |

(Continued)

*Primary Examiner* — Nam V Nguyen
(74) *Attorney, Agent, or Firm* — Dinsmore & Shohl LLP

(57) ABSTRACT

A medical device, with an operating element for triggering the medical device, includes a safety system for preventing an erroneous triggering of the device. The present invention encompasses a method for controlling the medical device including determining if an operating command is given by a person prior to the device's carrying out the command.

11 Claims, 3 Drawing Sheets

(56) References Cited

U.S. PATENT DOCUMENTS

| | | | |
|---|---|---|---|
| 6,551,276 B1* | 4/2003 | Mann et al. | 604/131 |
| 6,664,893 B1* | 12/2003 | Eveland et al. | 340/539.12 |
| 6,790,198 B1* | 9/2004 | White et al. | 604/151 |
| 6,889,074 B2* | 5/2005 | Uber et al. | 600/431 |
| 6,970,584 B2* | 11/2005 | O'Gorman et al. | 382/126 |
| 7,236,936 B2* | 6/2007 | White et al. | 705/3 |
| 7,264,148 B2* | 9/2007 | Tachibana | 235/375 |
| 7,285,117 B2* | 10/2007 | Krueger et al. | 606/34 |
| 7,291,126 B2* | 11/2007 | Shekalim | 604/67 |
| 7,578,802 B2* | 8/2009 | Hickle | 604/131 |
| 2002/0034321 A1 | 3/2002 | Saito et al. | |
| 2002/0038392 A1 | 3/2002 | De La Huerga | |
| 2002/0065685 A1 | 5/2002 | Sasaki et al. | |
| 2003/0050633 A1* | 3/2003 | Ellman et al. | 606/37 |
| 2003/0065308 A1 | 4/2003 | Villegas et al. | |
| 2007/0260489 A1 | 11/2007 | Sasaki et al. | |
| 2007/0260490 A1 | 11/2007 | Sasaki et al. | |

FOREIGN PATENT DOCUMENTS

| | | |
|---|---|---|
| WO | WO 99/10029 | 3/1999 |
| WO | WO 01/18332 A | 3/2001 |
| WO | WO 02/099393 A | 12/2002 |

* cited by examiner

DEVICE AND METHOD FOR IDENTIFYING A USER OF A MEDICAL DEVICE

CROSS-REFERENCE TO RELATED APPLICATION(S)

This application is a continuation of International Patent Application No. PCT/EP2004/005038, filed on May 11, 2004, which claims priority to German Application No. DE 103 25 106.5, filed on Jun. 3, 2003, the contents of both applications are incorporated in their entirety herein by reference

BACKGROUND

The present invention relates to medical devices and methods of making and operating or using them. In some embodiments, the invention relates to a device and a method for detecting whether a medical device, such as an injection device, an infusion device, a device for measuring the concentration of a specific substance, or any other medical function, delivery or measuring device, is being operated by a person. In some embodiments, the present invention relates to devices and methods for identifying a user or operator of a medical device on the basis of person-specific features such as, for example, biometrics or body-specific features, and to tying the operation or functions of a medical device to the identity of a person.

In the case of medical devices, such as injection devices, insulin pumps, or other substance delivery devices, or devices for performing measurements, it is often desired that the operation of such devices be carried out as unobtrusively as possible, the devices being carried, for example, in a pocket, on a belt or other support, and/or under the clothes of a user. If a bolus, a metered injection, or a single dose of medicant is to be triggered "blind", the controls, buttons or switches required for triggering should be easy to feel, so that they may be identified and actuated under clothes or when the device not visible to the user. When certain types of switches are used, e.g., touch-pads, push-buttons, etc., it is possible for a device to be triggered randomly and unintentionally by inadvertent actuation of the switch, for example, by contact with the belt or hand when putting on a safety belt, by inadvertent impact with an object, etc.

Furthermore, in the case of medical devices to be actuated by a switch or other user input there is the risk that persons not authorized to operate the device, such as children or persons inexperienced in handling the device, inadvertently or intentionally may trigger undesired actions of the device.

SUMMARY

In one embodiment of the present invention, a medical device is adapted to determine whether a person intended to activate the device and/or whether an anomaly or anomalous situation is present. In one preferred embodiment of the present invention, a medical device is adapted to establish whether a person attempting to actuate the device is authorized to do so, and/or whether a certain performance of the device is appropriate.

One object of the present invention is to provide a device and a method which make it possible for a medical device to be operated as safely and reliably as possible.

According to some embodiments, the device of the present invention comprises a medical device, such as an infusion device, a pump, an injection device, an injection pen, or a measuring device, for example. In some embodiments, the device may be used for measuring the proportion of a substance in a liquid, such as a blood sugar measuring device. Typically, the device has an operating element for triggering an action or performing a function, such as the administration of a substance by injection or infusion, for example in a metered dose or bolus. The device of the present invention further comprises, in some embodiments, a safety system for preventing unintentional, unauthorized or erroneous triggering of an action and/or to identify at least one person.

In general, the safety system according to the present invention may involve various functional principles that may be used individually or in combination in order to establish that a person has actuated the medical device, rather than the device being erroneously actuated by an unintentional impact, for example, or by any type of anomaly present in, on or affecting the medical device. Furthermore, the safety system may be designed in such a way that it determines whether the person who has actuated an operating element is authorized, and may block the selected operation if the person does not have authorization. This may prevent children or persons or patients who are not authorized from carrying out certain actions, like changing device settings, operating modes or parameters. Exemplary operations or functions include the dosage setting or amount of a substance to be administered, the time required between dosage delivery, the number of doses capable of being administered, or the identity of the persons authorized to operate the device. Such settings, operating modes, parameters or functions of a device and its use may be set or determined by an authorized physician or other health professional.

According to an embodiment of the present invention, if a person is identified, and one or more operating modes are stored as permissible or accessible for that person, the operating mode may be enabled. In another embodiment, a personal treatment plan or therapy program may be implemented upon identification of the person having an associated personal treatment plan or therapy program.

According to one embodiment, the safety system may comprise a force sensor, wherein a force acting on an operating element, such as a switch, is sensed and measured or assessed. In this case, for example, a limit value of a force to be applied at least and/or applied at most may be provided, so that an action is only triggered if the lower limit value is exceeded and/or not if the upper limit value is exceeded, whereby erroneous triggering, for example by slight impact, is avoided. Furthermore, it is possible to prescribe a time profile of a force distribution, with which the actual profile detected by the force sensor is compared with the force acting on the operating element. This may provide triggering of a desired action only when force distributions customary for an actuation by a finger, for example, are detected. Accordingly, "blind" dosage or bolus triggering or other operations resulting from inadvertent slight or severe impact may be prevented.

It is possible to use a temperature sensor as the safety system or a component thereof. In these embodiments, the temperature of an operating element may be measured during the actuation of the operating element. Accordingly, the sensor may determine whether the operating element has been actuated by a fingertip at body temperature, for example.

In some embodiments, an optical sensor may be used as the safety system or a component thereof. An optical sensor may scan the surface of a finger using laser beams in order to detect whether an operating element has been actuated by a finger. In another example, the optical sensor may be used to identify the fingerprint of the finger used for actuating the operating element, so that the fingerprint may be checked to determine if a person attempting to trigger a certain action is authorized to do so.

In general, so-called "fingerprint" sensors may be used as the safety system according to the invention or as a component thereof. Such fingerprint sensors may also be based on the measurement of a capacitive coupling between the surface of a finger and the sensor. In this example, a multiplicity of relatively small capacitance measuring devices are provided in an area on which a fingertip is to be placed, in order to detect the profile of the fingertip and consequently the fingerprint.

In a further example of the present invention, a touch screen may be used as the safety system or a component thereof, in which the screen also displays information concerning the operating state of the medical device to be operated, parameters or operating modes to be set, and/or patient information such as vital signs and measurement readings.

In another embodiment of the present invention, a transponder may be used as the operating element and/or the safety system or a component thereof. The transponder may be carried by a person and brought into the vicinity of the medical device where the transponder detects whether the medical device is to be enabled for operation by the person, for example. It may also be possible for the transponder to be implanted in the person, so that a unique assignment of the medical device to a specific person is ensured.

In general, the safety system according to the invention may be formed by one or more of the elements or components described above. It may be possible to increase operating safety by using two or more of the described safety components with one medical device or with a selected function or functions of a medical device. This may provide a safety system which is required to be activated or triggered in a prescribed manner in order to identify a user and to check their authorization.

According to some embodiments of the present invention, a safety system may be coupled to an operating element and may be designed and coupled such that, before the triggering of an action, a confirmation by an authorized user is required. In addition, it may be possible that, after requesting the triggering of a certain action, an optical and/or acoustic signal is output to indicate to a user that the action to be triggered must be confirmed before the action, such as the administration of a substance, is performed.

A combination of various safety or switching systems may be used for energy-saving operation(s) of a medical device, a first switch or a first safety system that uses little or no energy before actuation, such as a toggle switch, which, after actuation, switches on at least one further safety system or feature, which has an increased energy consumption in order to check the identity of a person operating the medical device. In some embodiments, the more energy-intensive safety system may be switched off or switch off automatically if identification is unsuccessful and/or after a prescribed time has elapsed in order to minimize the energy consumption, and consequently, for example, increase the lifetime of a battery provided in the medical device.

According to one embodiment, two operating elements, such as two switches that are attached at different positions of the medical device may be required to be actuated simultaneously or in a prescribed sequence. Providing two operating elements may also prevent a switch that is inadvertently pressed, for example by impact, to trigger and administer a dose or bolus. In particular, arranging operating elements on two sides of a medical device may prevent simultaneous exposure to an unintended action, force, or impact.

According to one embodiment, the safety system of the present invention may be capable of identifying at least one person. This may take place, for example, by the detection of one or more biometric person-specific features. A database storing patterns or information related to biometric data of individual persons may be provided in the medical device or separately from the device. According to certain embodiments, the medical device is capable of accessing a database via a suitable interface, such as a cable, radio, wireless, or infrared transmission, in order to have comparison or reference data available for comparison with the biometric data actually detected. This makes it possible for one or more persons to be unequivocally identified and to establish whether a person identified is authorized to carry out a desired action, or whether the performance of the action is blocked. In one example, biometric data, such as a fingerprint or a retinal pattern of a physician or other health professional authorized to set parameters of the medical device may be provided in such a database, so that only an authorized person may set the dose of a substance to be administered from the medical device. Certain actions may not be performed, or may only be partly performed by other persons not stored in the database or stored in the database and provided with a different access authorization. In some instances, it may also be possible that certain functions may be performed by all persons without identifying these persons or checking their authorization. In such a database, data serving for the identification of one or more persons may also be assigned specific authorization levels.

In the case of one or more sensors provided as a safety system, guides or aligning elements may be provided for aligning a person's identification objects with the device. This provides the device with the capability to obtain comparable data in the case of various measurements. For example, a guide for a finger may be provided, so that a fingertip to be placed on a sensor is always aligned approximately in the same way when it is placed on the sensor. This allows the speed of detection of the sensor to be increased, since additional computing time does not have to be used to check whether a detected fingerprint coincides with a reference fingerprint stored in a database if it is turned.

In some embodiments of the present invention, an optical and/or acoustic output device, such as an LED or a loudspeaker, may be provided, in order to indicate the operating state of the medical device or to draw attention to commands to be input.

In general, a safety system in accordance with the present invention may be provided in, at or in association with a medical device. It is also possible to provide a separate safety device or system, which may be operably coupled to the medical device and may serve for the detection of identification features, such as biometric data. In this case, the separate device may be coupled to the medical device by suitable means, e.g., cable, radio or infrared signals, or other types of wired or wireless transmissions, in order to transmit identification data or data for setting or operating the medical device. Similarly, data may also be transmitted from the medical device to the separate device, such as data concerning a current operating state or recorded data which specify the operation of the medical device over a prescribed period of time.

According to a further aspect of the present invention, the invention relates to a method for actuating a medical device, such as for triggering the administration of a substance and/or for carrying out a measurement, wherein a checking or identification method is performed. The checking or identification method is carried out to, for example, identify whether a person operating the medical device is actually authorized to carry out the desired operating action or to detect whether a person has triggered an operating action or whether the operating action was triggered inadvertently by an unintended event or impact, the performance of the action then not being commenced.

According to another embodiment of the invention, a medical device comprises an adjustable operating element configured to receive signals to deliver a therapeutic action and to carry out the therapeutic action corresponding to the signals received, and a safety system for receiving person-specific authorization signals for adjusting and/or enabling the operating element and/or for preventing erroneous adjustment and/or activation of the operating element. The medical device may be further configured to establish whether a person is actuating the operating element, and may be configured to identify whether the user is, for example, a health-care professional or non-health-care professional.

In some embodiments, the safety system associated with the medical device may be configured to include at least one of a force sensor, a temperature sensor, an optical sensor, a capacitive sensor, a fingerprint sensor, a touch screen and/or a transponder, and may be capable of identifying persons operating the device. The safety system may also be configured to receive a confirmation signal from an identified person that the operating element is to deliver a therapeutic action.

A medical device in accordance with the present invention may further comprise a database in which information such as information for the identification of at least one person and/or for the authorization level of an identified person is stored. A suitable processor and/or controller may be integrated or associated with the device as well.

An alignment device may also be included in the medical device and may be used to ensure that a biometric feature is detected with a body part in a prescribed positional relationship with respect to a sensor. In addition, or alternatively, the medical device may include an optical and/or acoustic output device for outputting an operating state of the device.

In some embodiments, a medical device in accordance with the present invention may further include a confirmation system or feature for user-confirmation of the intent to deliver the therapeutic action via the medical device. The confirmation feature may be required to receive two or more confirmation signals, where at least two of the confirmation signals are received from separate input locations on the medical device. The input locations may be medical device operating elements, may be required to receive the confirmation signals simultaneously, and/or may be required to be separated in a way that a user is unable to signal the input locations using a single finger or touch.

According to some embodiments of the present invention, the medical device in accordance with the present invention is configured as a personal medical device.

In another embodiment of the present invention, a safety system for use with a medical device includes a medical device operating element, and a safety mechanism associated with the medical device operating element for preventing erroneous actuation of the medical device operating element. The safety system may include an identification device for receiving user-specific identification data, and a securing mechanism providing a two or more securing levels, in which each of the two or more securing levels is releasable in response to receiving user-specific authorization data associated with one or more of the two or more securing levels, release of one or more of the securing levels providing a secure level of operation of the medical device operating element. According to a further embodiment, the identification device stores user-specific authorization data having associated user-specific identification data, processes and/or correlates received user-specific identification data with said stored user-specific authorization data having user-specific identification data, and sends said user-specific authorization data to said securing mechanism upon selected correlation of said received and stored user-specific identification data.

The present invention comprises a method for activating a medical device wherein, before an input command is carried out, the input command is checked to verify that the command was input by a person, and is checked to determine that the input command has been confirmed by the person. A further check may be performed to determine whether the identified person has a previously defined authorization. An activation command, according to one aspect medical device activation method, may be prevented from being input before a check is performed on the input command or the person operating the system. In addition, the system may carry out a person-specific program based on an identified person.

DETAILED DESCRIPTION OF THE DRAWINGS

With regard to fastening, mounting, attaching or connecting the components of devices of the present invention, unless specifically described as otherwise, conventional fasteners such as screws, rivets, toggles, pins and the like may be used. Other fastening or attachment means appropriate for connecting components include friction fitting, adhesives, welding and soldering, the latter particularly with regard to electrical or processing components or systems of the devices. Any suitable electronic, electrical, communication, computer or processing components may be used, including any suitable electrical components and circuitry, wires, wireless components, sensors, chips, boards, micro-processing or control system components, software, firmware, hardware, etc.

Figure 1:
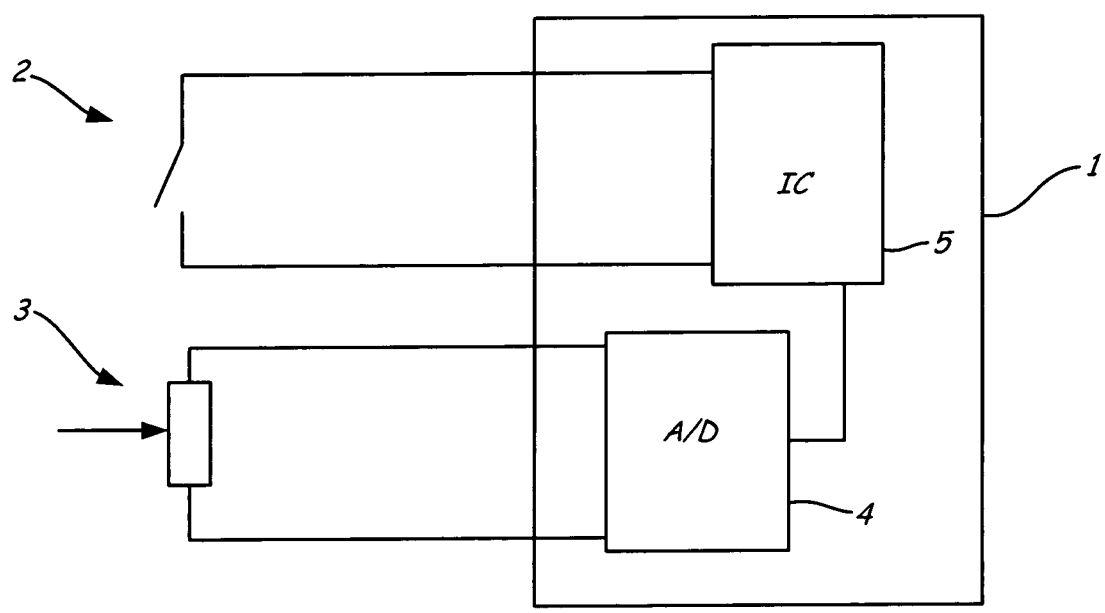
FIG. 1 is a schematic representation of an embodiment of the present invention.

FIG. 1 schematically shows an embodiment of an exemplary device according to the present invention, in this instance an insulin pump 1, which includes pump electronics 5, a suitable switch 2 (e.g. touch pad, push button, etc.) for operating the pump 1, and a force sensor 3 for preventing "blind" dosing or bolus triggering of the insulin pump 1. The switch 2 is operably coupled to the force sensor 3 in such a way that a pressure or a force acting on the switch 2 may be detected and may be compared with a prescribed force or a pressure profile after a conversion of the signals detected in analog form in the A/D converter 4 in the pump electronics 5. Consequently, inadvertent actuation of the switch, for example by unintended impact, may be detected, since in such a case the force typical for normal actuation or actuation by a finger is not present at the force sensor, i.e., does not coincide with a prescribed value or profile. Any suitable actuation characteristics may be involved, for example, a force distribution that is characteristic of manual actuation, a time profile of the force or pressure acting on the force sensor 3, etc. Prescribed values and/or profiles, may be stored, for example, in the pump electronics 5 or operatively associated therewith, so that the erroneous triggering of a bolus or dose may be detected and prevented.

Figure 2:
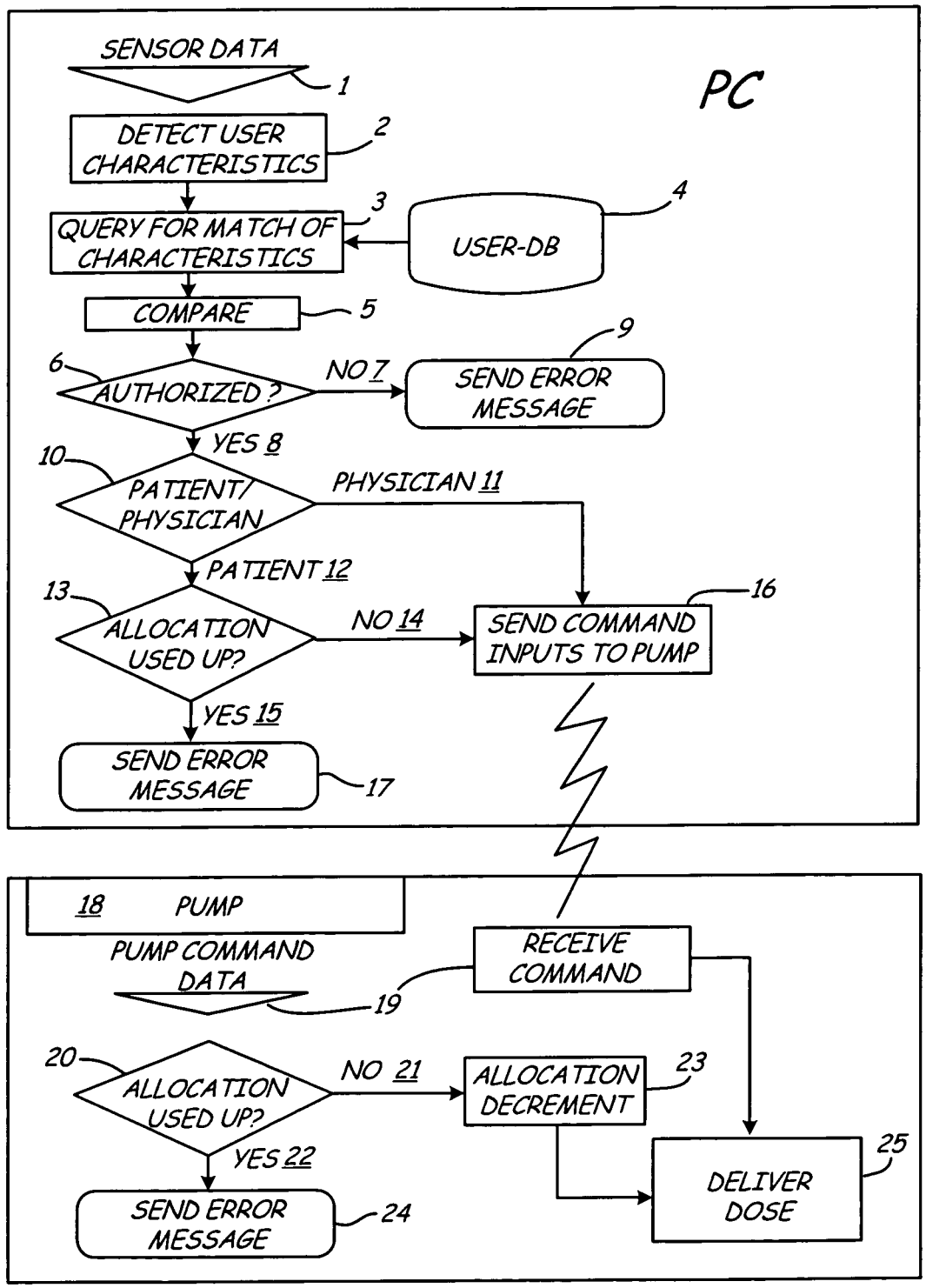
FIG. 2 is a flow diagram depicting operation of one embodiment of a method according to the present invention.

FIG. 2 is a diagram of the components and operation or operational flow of one embodiment of the present invention. It depicts a method for checking the authorization of an operator of a medical device, such as a pump for moving, dispensing or administering medical substances, e.g., insulin. In the embodiment shown, the checking of the authorization or authorization status of a user is carried out separately from the medical device by means of a suitable device, such as a PC with a sensor.

A sensor detects image data 1 of a user, in particular data suitable for the identification of a person, such as the structure of the retina, a fingerprint and/or any other suitable biometric features. Characteristic details 2, which also may be referred to as "minutiae", are read out from the detected image data, it being possible to detect characteristic patterns or features by means of an algorithm. Subsequently, a search or query 3 is carried out in a user database 4, in which corresponding features of authorized persons have previously been stored, to ascertain whether the features determined by the algorithm coincide with the features stored in the database. Correspondence is determined by comparing 5 the input data and the stored data, and the information is used to determine whether the user is authorized 6. If the user is authorized 8, the person operating the device is recognized from the image data detected by the sensor and authorization information may be made available, defining whether or not certain actions may be carried out by this person. If the user is not authorized 7, the device outputs an error message 9.

On the basis of this authorization information, it may be determined, for example, whether an input command is to be performed and, in the case of absent authorization, an error message may be output. If the person identified in this way is authorized to input the corresponding command, it may optionally be determined in a further step 10 whether the person identified is, for example, a physician 11 or a patient 12. So, for example, in the case of identification of a physician 11 who is entitled to input all commands, the command may be passed on directly to the pump 16 coupled to the PC.

If it is established that the PC was operated by a patient 12, it may be checked in a further step whether or not an allocation provided for the patient has already been used 13. If so 15, an error message 17 may be output, whereby, for example, patients may be prevented from administering too much painkiller to themselves. If the allocation has not yet been used 14, the patient is authorized to input the corresponding command, for example to trigger the administration of a specific dose of a substance by the pump, and the command may be transmitted to the pump 16.

In the pump 18 itself, the command 19 received may either be performed directly or a further check of the command input externally or directly into the pump may be carried out in the pump. So, for example, it is possible that whether or not a patient's allocation has already been used 20 may be checked again by or in the pump, and, dependent on this check, either an error message 24 is output when the allocation has been used 22 or the command 25 is performed. The allocation available to the patient reduced or decremented 23 by the dose given when the allocation has not been used 21 may be output or displayed, too.

It is also possible for information to be transmitted from the pump to the PC or other data storage device concerning the amount of substance given, allowing the PC or other data storage device to have data related to deliveries or infusions triggered directly at the pump.

Thus, it is possible to minimize the chances of administering an overdose and reduce the possibility of inadvertent operation of the medical device, for example by children or by accident. Reducing the chance of overdosage may be of interest when the device is being used to administer, for example, various pain reducing medications.

Figure 3:
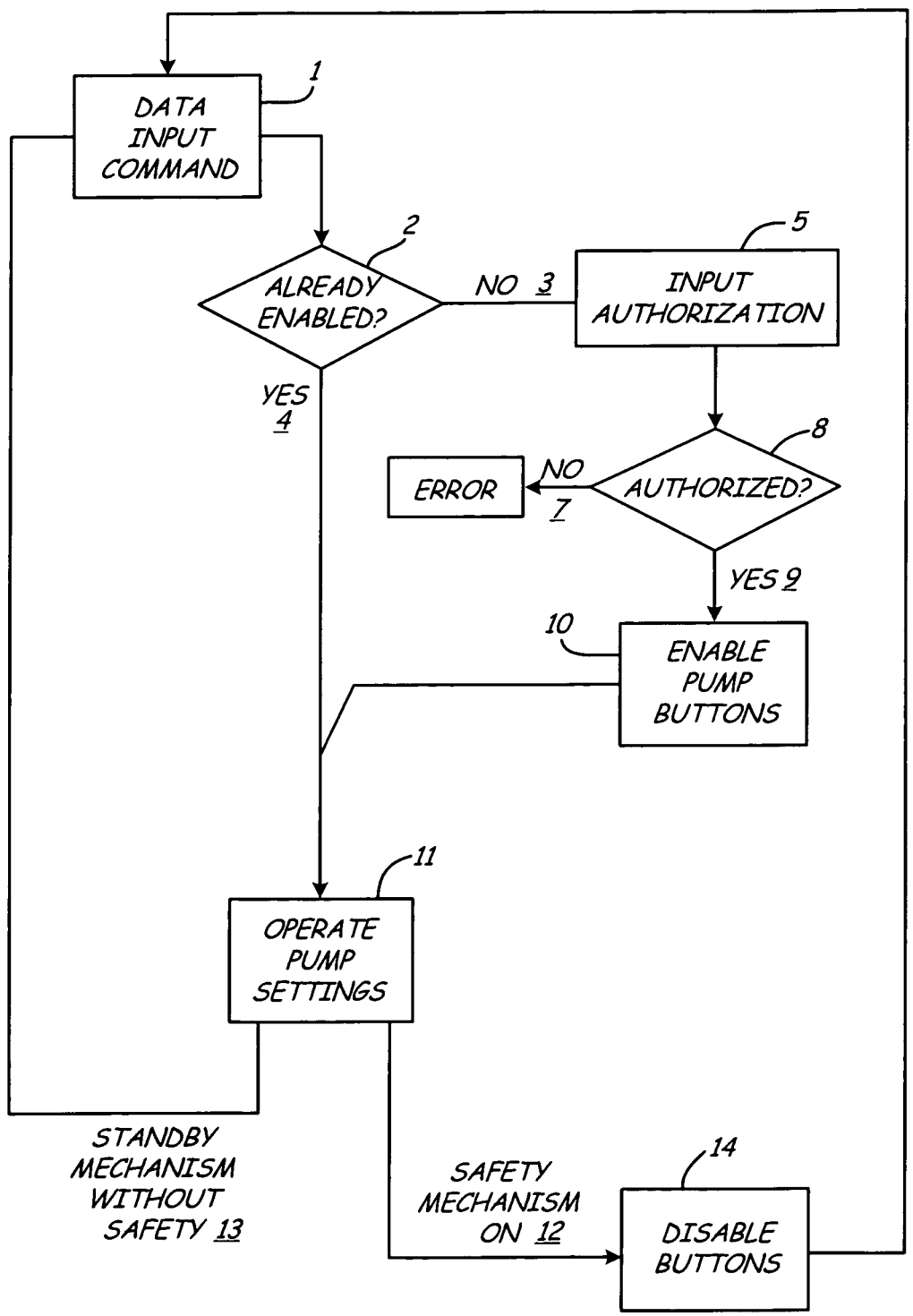
FIG. 3 is a flow diagram depicting operation of another embodiment of a method according to the present invention.

FIG. 3 shows a flow diagram of another embodiment of a method and components according to the present invention wherein an electronic identification device or electronic key is used to check the authorization of a person to operate a medical device, such as a pump.

A user inputs a command 1 into the medical device or into a device or peripheral which is operably coupled or may be coupled to the medical device and is recognized. The vehicle for inputting information may be, for example, a fingerprint or any other suitable biometric data, an enabling code and/or an electronic key. In one example, one electronic key per pump is provided, so that the pump only accepts the commands sent from the electronic key that is provided with a corresponding serial number or other correlative signal. A determination is made whether the pump is enabled 2. When the pump is enabled 4, and once identification and authorization checking of the user has taken place, the pump may operated 11 normally without further authorization checks being required. Optionally, a time restriction on the authorization to input commands may be provided, so that inadvertent enabling of a pump is automatically ended after the prescribed time. In an instance where the pump is not enabled 3, input authorization 5 is checked 8, and if the user is authorized 9, the pump inputs (e.g., buttons, etc.) are enabled 10. Alternatively, if the user is not authorized 7, an error message 6 is output. Furthermore, it is possible to actively or positively end the acceptance of commands input to the pump, so that, once the pump has been operated 11 by an authorized person, a safety mechanism 12 is initiated and further inputs to the pump may be prevented or disabled 14.

Consequently, the pump may be safeguarded, for example, against actuation by children or unauthorized users. Furthermore, it is also possible for a pump to be enabled without a safeguard or safety mechanism 13 by a user for use in an office, for example, and the safeguard to be switched on for use at home, for example to protect against unintentional activation by children.

Some embodiments of the present invention may include an authorization that allows all possible actions to be carried out, for example, in the form of a so-called "master key", which is made available to physicians, health professionals, or other persons, so that any pump or other device function or operational characteristic may be assessed, enabled or set by a physician.

Embodiments of the present invention, including preferred embodiments, have been presented for the purpose of illustration and description. They are not intended to be exhaustive or to limit the invention to the precise forms or steps disclosed. The embodiments were chosen and described to provide the best illustration of the invention and its practical application, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

INDEX

FIG. 2
1 Image data from the sensor
2 Read out minutiae with algorithm
3 Search in the database 4 User DB
5 Command input
6 Authorized?
7 no
8 yes
9 Output error message
10 Patient/physician?
11 Physician
12 Patient
13 Allocation used up?
14 no
15 yes
16 Pass on command to pump
17 Output error message
18 Pump
19 Command received
20 Allocation used up?
21 no
22 yes
23 Allocation decrement
24 Output error message
25 Perform command
FIG. 3
1 Input command
2 Already enabled?
3 no
4 yes
5 Input authorization
6 Error
7 no
8 Authorization given?
9 yes
10 Enable switches, e.g., buttons
11 Carry out settings
12 Switch on safeguard
13 Continue without safeguard
14 Disable switches, e.g., buttons

The invention claimed is:

1. A medical device for a patient comprising:
an operating element for triggering delivery of a therapeutic action of the medical device, wherein the operating element is a switch manually operable by a fingertip of the patient;
a safety system provided in the medical device and including:
a fingerprint sensor operatively coupled to the operating element and configured to generate fingerprint sensor signals relating to a manual actuation of the operating element;
a processor operatively coupled to the sensor such that the processor receives the sensor signals;
a memory coupled to the processor, wherein reference data that is characteristic of the manual actuation of the operating element is stored in the memory for retrieval by the processor;
wherein the processor is adapted to execute computer-implemented instructions to:
approximate whether the manual actuation of the operating element is an intentional act of a human based at least in part on a comparison of the sensor signals and the reference data, wherein the reference data is pattern data characteristic of the manual activation of the operating element by the fingertip of the patient, and
trigger the delivery of the therapeutic action when the comparison indicates the characteristic of the manual actuation of the operating element, wherein the safety system further comprises:
an identification device configured to transmit person-specific authorization signals, wherein the processor is operatively coupled to the identification device such that the processor receives the person-specific authorization signals, and
wherein reference information relating to authorized persons stored is stored in the memory for retrieval by the processor, and
wherein the processor is adapted to execute computer-implemented instructions to:
determine whether a user is authorized based at least in part on a comparison of the reference information and the received person-specific authorization signals, and
prevent at least one of adjusting the operating element, enabling the operating element, and activating the operating element if the user is not authorized.

2. The device as claimed in claim 1, wherein information for identification of at least one person and for an authorization level of an identified person is stored in the memory for retrieval by the processor, and wherein the processor is further adapted to execute computer-implemented instructions to:
establish an identity of a user of the device based at least in part on a comparison of the sensor signals and the information for identification of at least one person.

3. The device as claimed in claim 2, further comprising an alignment device configured to ensure that a biometric feature of a user of the device is detected with a body part of the user in a prescribed positional relationship with respect to the sensor.

4. The device as claimed in claim 1, further comprising at least one of an optical and acoustic output device for communicating the operating state of the device.

5. The device as claimed in claim 1, wherein the safety system is further configured to receive a confirmation signal from an authorized person that the operating element is to deliver the therapeutic action.

6. The device as claimed in claim 1, wherein information relating to an authorization level of particular authorized persons is stored in the memory for retrieval by the processor.

7. The device as claimed in claim 1, further comprising an alignment device configured to ensure that a biometric feature is detected with a body part in a prescribed positional relationship with respect to the fingerprint sensor.

8. The device as claimed in claim 1, further comprising at least one of an optical and an acoustic output device for communicating the operating state of the device.

9. The device as claimed in claim 1, wherein the medical device comprises a personal medical device configured to be worn or carried on the body of a patient.

10. A medical device for a patient comprising:
first and second operating elements for triggering an action of the medical device and arranged at different positions on the medical device, wherein the second operating element is a switch manually operable by a fingertip of the patient; and
a safety system provided in the medical device including:
a fingerprint sensor operatively coupled to the first operating element and configured to generate fingerprint sensor signals relating to actuation of the first operating element;
a force sensor operably coupled to the second operating element such that a pressure or force acting on the second operating element is detected by the force sensor;
a processor operatively coupled to both the fingerprint sensor and the force sensor such that the processor receives the fingerprint sensor signals from the fingerprint sensor and a pressure or force signal from the force sensor;

a memory coupled to the processor, wherein fingerprint reference data and pattern data are stored in the memory for retrieval by the processor, wherein the pattern data is characteristic of a manual activation of the second operating element by a human finger;

wherein the processor is adapted to execute computer-implemented instructions to:

determine whether actuation of the first operating element is an intentional act of a human based at least in part on a comparison of the fingerprint sensor signals and the fingerprint reference data, determine whether actuation of the second operating element is an intentional act of a human based at least in part on a comparison of the pressure or force signal and the pattern data, wherein activation of the first and second operating elements simultaneously or in a prescribed sequence will cause the action of the medical device upon the processor determining that the actuation of the first and second operating elements is an intentional action, wherein an output signal is provided by the safety system to indicate that the actuation of the operating elements simultaneously or in the prescribed sequence is required before the action to be performed by the medical device is performed.

11. The device as claimed in claim 10, wherein said fingerprint sensor is configured to scan the surface of an object actuating the operating element, and wherein the processor is adapted to execute computer-implemented instructions to determine whether the object actuating the first operating element has been actuated using is a human finger.

* * * * *

UNITED STATES PATENT AND TRADEMARK OFFICE
CERTIFICATE OF CORRECTION

| | |
|---|---|
| PATENT NO. | : 8,717,141 B2 |
| APPLICATION NO. | : 11/293468 |
| DATED | : May 6, 2014 |
| INVENTOR(S) | : Andreas Eberhart et al. |

It is certified that error appears in the above-identified patent and that said Letters Patent is hereby corrected as shown below:

In the Specification

Col. 1, Line 38-39,
  "be identified and actuated under clothes or when the device not visible to the user. When certain types of switches are" should read
  --be identified and actuated under clothes or when the device is not visible to the user. When certain types of switches are--;

Col. 6, Line 14,
  "command, according to one aspect medical device activation" should read
  --command, according to one aspect of the medical device activation--;

Col. 8, Lines 20-21,
  "tion checking of the user has taken place, the pump may operated 11 normally without further authorization checks" should read
  --tion checking of the user has taken place, the pump may be operated 11 normally without further authorization checks--; and In the Claims Col. 12, Line 16, Claim 11,
  "element has been actuated using is a human finger." should read
  --element has been actuated using a human finger.--.

Signed and Sealed this
Twenty-fourth Day of February, 2015

Michelle K. Lee
*Deputy Director of the United States Patent and Trademark Office*